United States Patent [19]

Zeeck et al.

[11] Patent Number: 5,118,882

[45] Date of Patent: Jun. 2, 1992

[54] STREPTENOLS FROM STREPTOMYCETES, AND THE PREPARATION AND USE THEREOF

[75] Inventors: Axel Zeeck, Göttingen; Susanne Grabley, Königstein/Taunus; Joachim Wink, Offenbach; Peter Hammann, Kelkheim; Carlo Giani, Frankfurt am Main; Pia Kricke-Helling, Bovenden, all of Fed. Rep. of Germany

[73] Assignee: Hoechst Aktiengesellschaft, Frankfurt am Main, Fed. Rep. of Germany

[21] Appl. No.: 482,885

[22] Filed: Feb. 22, 1990

[30] Foreign Application Priority Data

Feb. 25, 1989 [DE] Fed. Rep. of Germany ....... 3905930

[51] Int. Cl.$^5$ ............................................ C07C 33/035
[52] U.S. Cl. .................................... 568/857; 568/415; 435/155; 435/183
[58] Field of Search ................................ 568/415, 857

[56] References Cited

PUBLICATIONS

Isoe et al., Chem Abst., vol. 102, #149,404s (1985).
Narita et al., Chem Abst., vol. 109, #169872r (1988).
Narita et al., Chem. Abst., vol. 107, #5734e (1987).
Arnone et al., Chem. Abst., vol. 110, #111,373h (1989).
Keller-Schierlein et al., "(3S, 8E)-1,3-Dihydroxy-8-decen-5-5 on, ein Stoffwechselprodukt von *Streptomyces fimbriatus*" (Millard und Burr 1926), *Helvetica Chimica Acta*-vol. 66, pp. 1253–1261.
Mizutani, S. et al., "Biological Activities of IC201 ((3S,8E)-1,3,-Dihydroxy-8-Decen-5-One), A Low Molecular Weight Immunomodulator Produced by *Streptomyces*", *J. Antibiotics* vol. 42, No. 6, Jun. 1989.
Organic Chemistry, Morrison and Boyd (eds.); p. 774; 1987.

*Primary Examiner*—James H. Reamer
*Attorney, Agent, or Firm*—Finnegan, Henderson, Farabow, Garrett and Dunner

[57] ABSTRACT

Novel streptenols with pharmacological activity, in particular with HMG-CoA-reductase inhibiting activity, can be isolated from the nutrient broth of streptomycetes. These compounds can also be used as synthesis unit for the production of mevilonin analogues.

1 Claim, No Drawings

STREPTENOLS FROM STREPTOMYCETES, AND THE PREPARATION AND USE THEREOF

DESCRIPTION

Streptenols are hydroxylated aliphatic compounds which are synthesized in nature essentially by streptomycetes.

A molecule of this substance class has already been described [Keller-Schierlein et al. Helvetica Chimica Acta 66, 1253 (1983)], but it has no biological action against bacteria and only a very low inhibitory action against individual fungi. The compound is synthesized by Streptomyces fimbriatus. Fermentation of the streptomycete DSM 4356 resulted in two novel compounds of this group in addition to the streptenol which was already known.

These novel compounds inhibit the hydroxymethylglycosyl (HMG)-CoA. reductase of the lipid metabolism and can be employed as synthesis units, in particular for the preparation of mevilonin analogues, the most effective HMG-CoA reductase inhibitors.

The invention therefore relates to:
1. The compound of the general formula I,

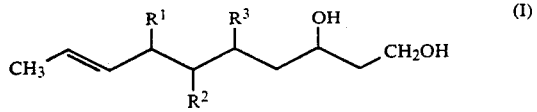
(I)

in which
$R^1$ and $R^2$ represent hydrogen or together form a double bond and $R^3$ represents an oxo group or a hydroxyl group.

2. A process for the preparation of the compound characterized under 1., of the general formula I, which process comprises culturing a strain of the genus Streptomyces in a liquid culture medium until said compound is accumulated in the liquid culture medium.

3. The use of the compound characterized under 1., of the general formula I, as an HMG-CoA reductase inhibitor or as a syntheseis unit for the preparation of mevilonin analogues.

In what follows, the invention is described in detail, in particular in its preferred embodiments The invention is furthermore defined in the claims.

The compound of the general formula I is prepared in particular by a Streptomycete strain which had been deposited at the Deutsche Sammlung von Mikroorganismen [German Collection of Microorganisms] in compliance with the provisions of the Budapest Convention under the number DSM 4356.

The spore morphology of Streptomyces spec. DSM 4356 can be characterized as follows:
Spore colour: grey
Spore chain: close spirals
Spore surface spiny It is also possible to use the mutant and variants in each case in place of the mentioned strain if they synthesise the compound of the general formula I. Such mutants can be generated in a manner known per se by physical means, for example irradiation, such as ultra-violet rays or X-rays, or chemical mutagens, such as, for example, ethyl methane sulfonate (EMS), N-methyl-N'-nitro-N-nitroso-guanidine (MNNG) or 2-hydroxy-4-methoxy-benzophenone (MOB).

Suitable as a preferred carbon source for the aerobic fermentation are carbohydrates and sugar alcohols which can be assimilated, such as glucose, lactose or mannitol, as well as carbohydrate-containing natural products, such as malt extract. Preferred suitable nitrogen-containing nutrients are:

Amino acids, peptides and proteins as well as their degradation products, such as peptones or tryptones, furthermore meat extracts, ground seeds, for example of maize, wheat, beans, soya or of the cotton plant, distillers'residues from alcohol production, meat meals or yeast extracts, and also ammonium salts and nitrates. The liquid culture medium can furthermore contain for example chlorides, carbonates, sulfates or phosphates of the alkali metals or alkaline earth metals, iron, zinc and manganese, as additional inorganic salts.

The compound of the general formula I is particularly advantageously formed in a liquid culture medium which contains soya flour and mannitol in concentrations of 0.5 to 6 % in each case, preferably 1 to 4 %, based on the weight of the total liquid culture medium.

The fermentation is aerobic, i.e. for example, submerged in shake flasks or fermenters with shaking or stirring, if appropriate with the introduction of air or oxygen. The fermentation can take place in a temperature range of about 18° to 35° C., preferably at about 25° to 30° C., in particular at 28° to 30° C. The microorganism is cultured under the conditions mentioned until the stationary phase is reached, for about 60 to 120 hours, preferably 70 to 75 hours.

The microorganism is expediently cultured in several steps, that is to say, one or more precultures are first established in a liquid nutrient medium, with which then the actual production medium, the main culture, is innoculated, for example in a volumetric ratio of 1:10. The preculture is obtained for example by innoculating a liquid culture medium with a spore-producing mycelium and allowing the culture to grow for about 48 to 72 hours. The spore-producing mycelium can be obtained by growing the strain for about 7 days on a solid or liquid culture medium, for example yeast-malt agar.

The course of the fermentation can be monitored with the aid of the pH of the culture, the volume of the mycelium, by thin-layer chromatography or assays of the biological activity.

The streptenols of the general formula I are isolated from the culture medium by known methods, allowing for the chemical, physical and biological properties of the products. Streptenols of the general formula I are present in the mycelium and the culture liquid. They can be extracted from the unfiltered culture liquid with an organic solvent which is not, or only sparingly, miscible with water, such as chloroform or ethyl acetate. Since only a small amount of the said streptenols is present in the mycelium, it is expedient to separate the culture liquid from the mycelium, for example by centrifugation or filtration, expediently with the addition of filtering auxiliaries. The compound of the general formula I can then be isolated from the supernatant or filtrate, advantageously in the slightly acid to neutral pH range, preferably at pH 6 to 7. For this purpose, organic solvents which are sparingly, or not, miscible with water can be used, in particular chlorinated hydrocarbons, such as chloroform or methylene chloride, or esters, such as ethyl acetate or acetone.

Instead of by extraction, the streptenols can also be isolated from the culture liquid by adsorption on commercially available absorber resins. It has also proven advantageous to dry said fermenter contents, for example by spray-drying or freeze drying.

The usual process steps such as chromatography or gelfiltration, can be used to isolate the pure streptenols. Silica gel chromatography has proven particularly advantageous, a mixture of ethyl acetate and hexane being used as the eluent, in a volumetric ratio of for example 1:2.

The streptenols of the general formula I are oily and readily soluble in methanol, acetone, dimethyl sulfoxide, dioxane and chloroform, but sparingly soluble in water and not soluble in alkanes.

The streptenols according to the invention inhibit HMG-CoA reductase and can therefore reduce in vivo the amount of cholesterol in the organism. Furthermore, the compounds can also be used for the synthesis of mevilonin analogues.

EXAMPLES

1. Fermentation of the producing strain DSM 4356
   a) Preparation of a spore suspension of the producing strain: 100 ml of liquid culture medium (4 g of yeast extract, 10 g of malt extract, 4 g of glucose, 1 l of tap water, pH before sterilization: 7.3) contained in a 500 ml Erlenmeyer flask are innoculated with the strain and the culture is incubated for 72 hours at 27° C. on a rotary shaker at 120 RPM. 20 ml of the culture liquid are then uniformly distributed in a 500 ml Erlenmeyer flask containing the culture medium of the abovementioned composition to which 20 g agar/l had been added for solidification, and the liquid is subsequently decanted off. The cultures are incubated for 10 to 14 days at 27° C. The spores of one flask which have formed after this period are rinsed off with 500 ml of deionized water containing one drop of a commercially available non-ionic surfactant, and the spore suspension is immediately used or stored at −22° C.
   b) Production of a culture or preculture of a producing strain in Erlenmeyer flasks:
   A 500 ml Erlenmeyer flask containing 100 ml of a liquid culture medium composed of 2% of meat meal, 10% of malt extract, 1% calcium carbonate and water to 100% (pH 7.2 before autoclaving) is innoculated with a culture grown on slanted agar or with 0.2 ml of spore suspension, and the culture is incubated at 27° C. on a rotary shaker at 120 RPM. Maximum production of the desired substance is reached after 72 hours. 10 and 100 l fermenters are innoculated with 5% of a 48 hour old submerged culture of the same liquid culture medium.
   c) Preparation of the streptenols:
   A 10 l ferment is operated under the following conditions:

| Culture medium: | 2% of mannitol |
| --- | --- |
| | 2% of soya meal |
| | pH 7.2 |
| Incubation time: | 72 hours |
| Incubation temperature: | 30° C. |
| Stirring rate: | 250 rpm |
| Aeration: | 4 l of air/min. |

The development of foam can be suppressed by repeatedly adding a few drops of an ethanolic polyol solution. The production maximum is reached after about 70 hours (pH=5.3). The yields are about 20 mg/l.

2. Isolation of the streptenols

After the producing strains have been fermented, the culture liquid is filtered with the addition of 2% of Celite as a filtering auxiliary. The mycelium is extracted using ethyl acetate and the organic phase is evaporated. The culture filtrate is dried, and the residue is extracted using ethyl acetate. The crude product is chromatographed on a silica gel column (silica gel 60; Macherey-Nagel) using ethyl acetate/hexane (1:2; v:v).

3. Characterization of streptenols
   a) Characterization of compound:

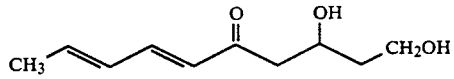

$^{13}$C-NMR (CDCl$_3$, 75 MHz): δ=18.8; 37.9; 46.5; 61.1; 68.0; 127.7; 130.2; 141.5; 144.3; 200.9 ppm.

b) Characterization of the compound

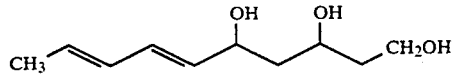

$^{13}$C-NMR (CDCl$_3$, 75 MHz): δ=18.2; 41.1; 45.7; 60.1; 66.6; 69.7; 129.8; 130.9; 132.3; 134.8 ppm.

c) Characterization of the compound:

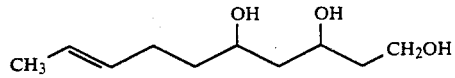

$^{13}$C-NMR (CDCl$_3$, 75 MHz): δ=17.9; 36.0; 37.0; 38.3; 42.6; 61.9; 69.1; 69.8; 125.6; 130.7 ppm.

4. Inhibition of cholesterol biosynthesis

The biological effectiveness of the compound of the formula I was determined using cell cultures of cell line HEP-G2. For this purpose, monolayers of HEP-G2 cells were preincubated for one hour in a lipo-protein-free culture medium containing appropriate concentrations of the test substances; after the $^{14}$C-labeled precursor $^{14}$C-(sodium acetate) has been added, incubation is continued for three hours. After this, a portion of the cells are subjected to alkaline hydrolysis, an internal standard of $^3$H-cholesterol having been added previously. The lipids of the hydrolysed cells are extracted using chloroform/methanol. Support-cholesterol is added, and this lipid mixture is then separated by means of preparative thin-layer chromatography; the cholesterol band is made visible and then isolated, and the amount $^{14}$C-cholesterol which has been formed from the $^{14}$C-precursor is determined scintigraphically. The control is used for comparing the inhibitory action of a test preparation which has been added, so that cholesterol biosynthesis inhibition can be indicated directly at a certain molar concentration of the test preparation in the medium. In aliquots of the cell culture, the intactness of the cell culture and lack of damage to cells by the influence of preparations is assessed morphologically (in an optical microscope) and biochemically by determining the amount of lactate dehydrogenase in the incubation medium.

The standard preparation used was lovastatin. Various lovastatin concentrations were employed, and the concentration at which 50% of the cholesterol synthesis was inhibited was determined (IC$_{50}$ value). The IC$_{50}$ value for lovastatin was $2\times10^{-8}$ M. The IC$_{50}$ values for streptenol 3a to 3c were within the same concentration range.

We claim:
1. A compound of the general formula I,

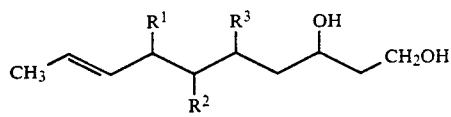 (I)
in which
R¹ and R² represent hydrogen or together form a double bond, and
R³ is a hydroxyl group.
* * * * *
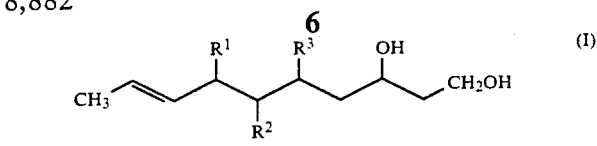 (I)
in which
R¹ and R² represent hydrogen or together form a double bond, and
R³ is a hydroxyl group.
* * * * *